US006439238B1

(12) United States Patent
Brenzel et al.

(10) Patent No.: US 6,439,238 B1
(45) Date of Patent: Aug. 27, 2002

(54) SNORING DIAGNOSTIC AND TREATMENT

(75) Inventors: Michael P. Brenzel, St. Paul; Hugh Qinghong Zhao, Andover, both of MN (US)

(73) Assignee: Pi Medical, Inc., St. Paul, MN (US)

( * ) Notice: Subject to any disclaimer, the term of this patent is extended or adjusted under 35 U.S.C. 154(b) by 95 days.

(21) Appl. No.: 09/608,651

(22) Filed: Jun. 30, 2000

(51) Int. Cl.$^7$ ............................................... A61B 19/00
(52) U.S. Cl. ...................................... 128/898; 600/529
(58) Field of Search ............................... 600/300, 301, 600/529; 128/897–925, 848

(56) References Cited

U.S. PATENT DOCUMENTS

| | | | |
|---|---|---|---|
| 4,830,008 A | | 5/1989 | Meer |
| 5,284,161 A | | 2/1994 | Karell |
| 5,718,702 A | | 2/1998 | Edwards |
| 5,792,067 A | | 8/1998 | Karell |
| 5,804,211 A | * | 9/1998 | Robertson et al. .......... 424/434 |
| 5,900,245 A | * | 5/1999 | Sawhney et al. ............ 424/426 |
| 6,161,541 A | * | 12/2000 | Woodson ..................... 128/848 |

FOREIGN PATENT DOCUMENTS

EP    0 706 808 A1    4/1996

OTHER PUBLICATIONS

Hoffstein et al, Reduction in Snoring with Phosphocholinamin, a Long Acting Tissue–Lubricating Agent, 1987, Am J Otolaryngol, Jul.–Aug.; 8(4): 236–40.*
LaFrentz, J.R.L. et al., "Palatal stiffening techniques for snoring in a novel canine model", *ARO Abstracts*, vol. 22, Abstrct No. 499, pp. 125–126 (Feb. 13–18, 1999).
C. Lorenz, "If he Snores—what can you do about it?", Today's Woman, Jul. 1948, p. 112.
Dalmasso, F. et al., "Snoring: analysis, measurement, clinical implications and applications", *Eur Respir J.*, vol. 9, pp. 146–159 (1996).
Harries, P.G., et al, "Review Article: The surgical treatment of snoring", *The Journal of Laryngology and Otology*, vol. 110, pp. 1105–1106 (Dec. 1996).
Huang, L. et al. "Biomechanics of snoring", *Endeavour*, vol. 19, No. 3, pp. 96–100 (1995).
Schwartz, R. et al., "Effects of electrical stimulation to the soft palate on snoring and obstructive sleep apnea", *The Journal of Prosthetic Dentistry*, vol. 76, No. 3, pp. 273–281 (Sep. 1996).
Brochure, "What causes Snoring?", *Minneapolis Otolaryngology*, 2 pgs.
Brochure, "Our Diagnostic Procedures are a Snap!®", *Snap Laboratories*, 4 pgs.
Brochure, "Snoreless™", *Nutrition For Life International*, 2 pgs. (Dec. 1999).
Brochure, "Snore–Free Nights–Guaranteed!",*Your Health News*, 2 pgs.
U.S. application Ser. No. 09/513,432, filed Feb. 25, 2000.

* cited by examiner

Primary Examiner—Eric F. Winakur
Assistant Examiner—David McCrosky
(74) Attorney, Agent, or Firm—Merchant & Gould P.C.

(57) ABSTRACT

A diagnostic method is for indicating a patient's susceptibility to treatment of snoring by stiffening a region of the patient's a naso-pharyngeal area includes applying a stiffening agent to an outer surface of the region of the nasopharyngeal area. The stiffening agent is left in place on the outer surface for at least a temporary period of time. During the temporary period of time, observation is made of any abatement of snoring.

17 Claims, 6 Drawing Sheets

US 6,439,238 B1

SNORING DIAGNOSTIC AND TREATMENT

I. BACKGROUND OF THE INVENTION

1. Field of the Invention

This invention pertains to a diagnostic and treatment for snoring. More particularly, this invention pertains to a method for diagnosing a patient's susceptibility to a snoring treatment by temporarily stiffening tissue suspected of contributing to snoring.

2. Description of the Prior Art

Snoring has received increased scientific and academic attention. One publication estimates that up to 20% of the adult population snores habitually. Huang, et al., "Biomechanics of Snoring", *Endeavour*, p. 96–100, Vol. 19, No. 3 (1995). Snoring can be a serious cause of marital discord. In addition, snoring can present a serious health risk to the snorer. In 10% of habitual snorers, collapse of the airway during sleep can lead to obstructive sleep apnea syndrome. Id.

Notwithstanding numerous efforts to address snoring, effective treatment of snoring has been elusive. Such treatment may include mouth guards or other appliances worn by the snorer during sleep. However, patients find such appliances uncomfortable and frequently discontinue use (presumably adding to marital stress).

Electrical stimulation of the soft palate has been suggested to treat snoring and obstructive sleep apnea. See, e.g., Schwartz, et al., "Effects of electrical stimulation to the soft palate on snoring and obstructive sleep apnea", *J. Prosthetic Dentistry*, pp. 273–281 (1996). Devices to apply such stimulation are described in U.S. Pat. Nos. 5,284,161 and 5,792,067.

Surgical treatments have been employed. One such treatment is uvulopalatopharyngoplasty ("UPPP"). In this procedure, so-called laser ablation is used to remove about 2 cm of the trailing edge of the soft palate thereby reducing the soft palate's ability to flutter between the tongue and the pharyngeal wall of the throat. The procedure is frequently effective to abate snoring but is painful and frequently results in undesirable side effects. Namely, removal of the soft palate trailing edge comprises the soft palate's ability to seal off nasal passages during swallowing and speech. In an estimated 25% of uvulopalatopharyngoplasty patients, fluid escapes from the mouth into the nose while drinking. Huang, et al., supra at 99. UPPP is also described in Harries, et al., "The Surgical treatment of snoring", *Journal of Laryngology and Otology*, pp. 1105–1106 (1996) which describes removal of up to 1.5 cm of the soft palate.

Huang et al. describe treating snoring by stiffening the soft palate through laser scarring. This includes laser scarring of the surface of the soft palate. Another technique involves RF ablation of the tissue of the soft palate. Available through Somnus Medical Technologies, Inc., this technique inserts a needle into the soft palate. The tip of the needle generates RF energy to ablate and scar the soft palate tissue. This technique is illustrated in U.S. Pat. No. 5,718,702. Debate continues as to the permanency and efficacy of such treatments.

A preferred technique is disclosed in commonly assigned and co-pending U.S. patent application Ser. No. 09/513,432. According to certain embodiments of that application, permanent implants are placed in the soft palate to add stiffness to the soft palate.

Since snoring can be attributed to vibratory motion at different locations in the naso-pharyngeal area, a snoring treatment may not be as effective as possible. For example, a soft palate treatment will not be effective if offensive snoring sounds are due principally to vibratory motion in the nasal concha or the pharyngeal wall.

Efforts to isolate or determine the contributory nature of snoring location include measuring the frequency of the snoring sound. Empirical data reveal that the palatal snoring produces a different pitch than, for example, nasal snoring. One product and service that is used to record snoring and compare to empirical data for such an assessment is available from Snap Industries, LLC, Glenview, Ill., USA. The acoustics of snoring is described in Dalmasso et al., "Snoring: analysis, measurement, clinical implications and applications", *European Respiratory Journal*, pp. 146–159 (1996).

Another diagnosis technique to identify a location of airway obstruction is to insert a tube into the throat. Sonic signals are sent down the tube and reflected waves are noted and recorded. Location of obstruction of the airway can be determined by measuring the reflected sound wave.

Notwithstanding the foregoing, a continuing need exists to diagnose snoring. For example, empirical data is mixed and only partially reliable. Under the previous techniques, the diagnosis locates a snoring source but cannot accurate predict the efficacy of a treatment for a particular person. Further, the techniques can be expensive requiring expensive equipment as well as patient discomfort.

II. SUMMARY OF THE INVENTION

According to a preferred embodiment of the present invention, a diagnostic method is disclosed for indicating a patient's susceptibility to treatment of snoring by stiffening a region of the patient's a naso-pharyngeal area. The method includes applying a stiffening agent to an outer surface of the region of the naso-pharyngeal area. The stiffening agent is left in place on the outer surface for at least a temporary period of time. During the temporary period of time, observation is made of any abatement of snoring. According to an alternative embodiment, the agent is left in place for extended periods or re-applied as desired for a snoring treatment.

III. BRIEF DESCRIPTION OF THE DRAWINGS

IV. DESCRIPTION OF A PREFERRED EMBODIMENT

Referring now to the several drawing figures, in which identical elements are numbered identically throughout, a description of a preferred embodiment of the present invention will now be provided.

Figure 1:
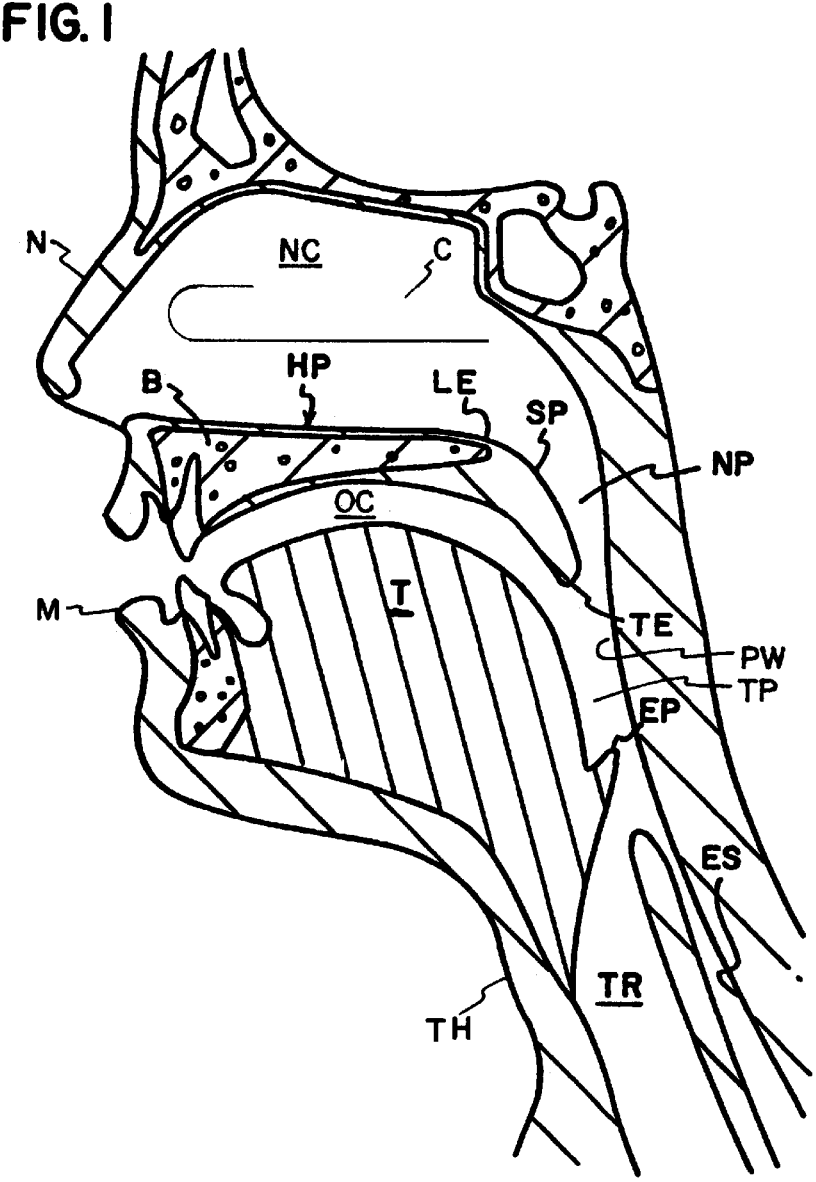
FIG. 1 shows, in cross-section, a naso-pharyngeal area of an untreated patient.
Figure 2:
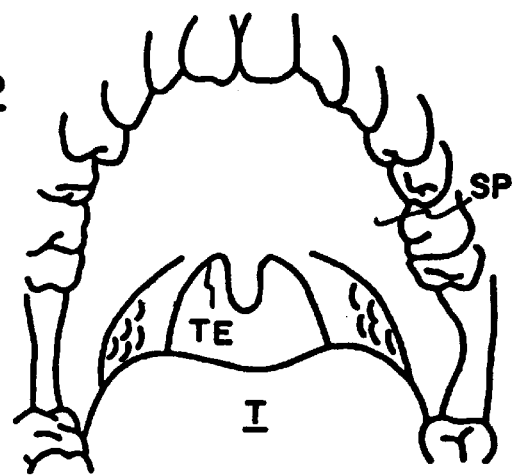
FIG. 2 shows a soft palate viewed through an open mouth of the untreated patient of FIG. 1.

FIG. 1 shows, in cross-section, a naso-pharyngeal area of an untreated patient. FIG. 2 shows a soft palate SP viewed through an open mouth of the untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area of the patient with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces means surfaces exposed to air. Both the upper and lower surfaces of the soft palate SP are outer surfaces.

Snoring can result from vibration of any one of a number of surfaces or structures of the naso-pharyngeal area. Most commonly, snoring is attributable to vibration of the soft palate SP. However, vibratory action of the nasal concha C and the pharyngeal wall PW can also contribute to snoring sounds. It is not uncommon for vibratory action from more than one region of the naso-pharyngeal area to contribute to snoring sounds.

Snoring treatments typically act upon a potential vibratory site of the naso-pharyngeal area. It is possible a treated site can be treated and snoring continues because the treated site was, in fact, not the source of offending snoring sounds or there are other sites contributing to snoring. Also, not all contributing sites need be treated. The offensive nature of snoring is subjective. A non-snoring spouse may find some degree of snoring abatement acceptable by treating only a selected one of a number of areas contributing to snoring. Therefore, it is desirable to test for efficacy of treatment of a particular site.

According to the diagnostic of the present invention, a stiffening agent is applied to an outer surface of a region of the naso-pharyngeal area. The agent is left in place to permit observation of any abatement of snoring. The present invention can also be used as a treatment by leaving the agent in place or re-applying the agent as desired.

While most of the present discussion will describe application of a stiffening agent to a lower surface of the soft palate SP, it will be appreciated the present invention is applicable to other regions of the naso-pharyngeal area including the nasal concha C and the pharyngeal wall PW.

Figure 3:
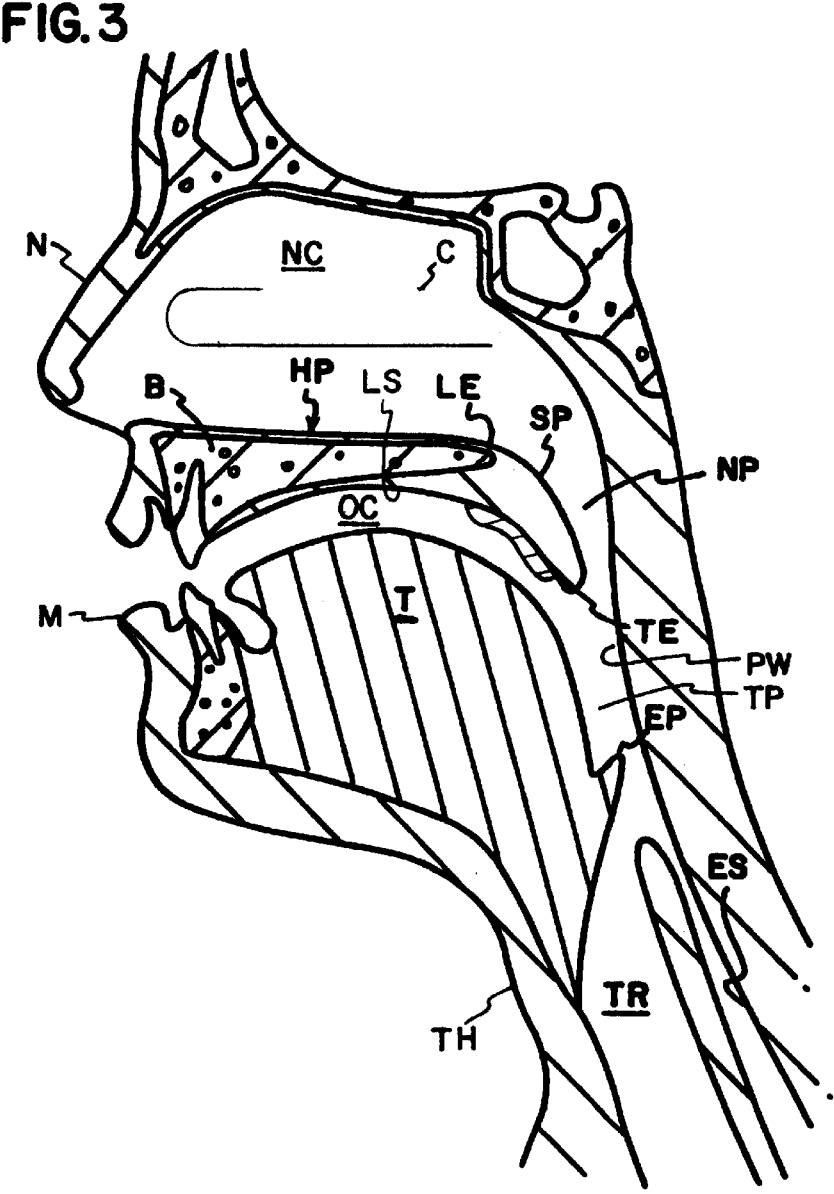
FIG. 3 is the view of FIG. 1 with the patient treated with a stiffening coating applied to a lower surface of the soft palate.
Figure 4:
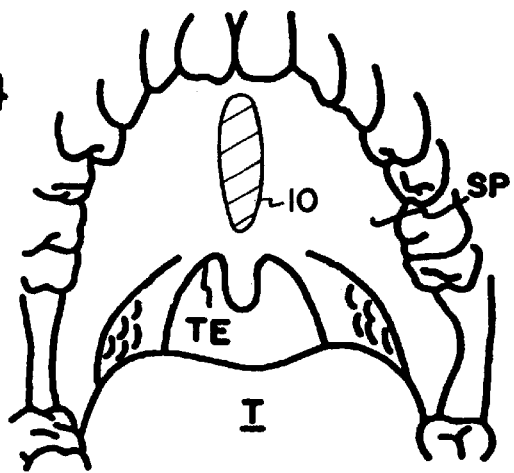
FIG. 4 is the view of FIG. 2 showing the coating treatment of FIG. 3.
Figure 5:
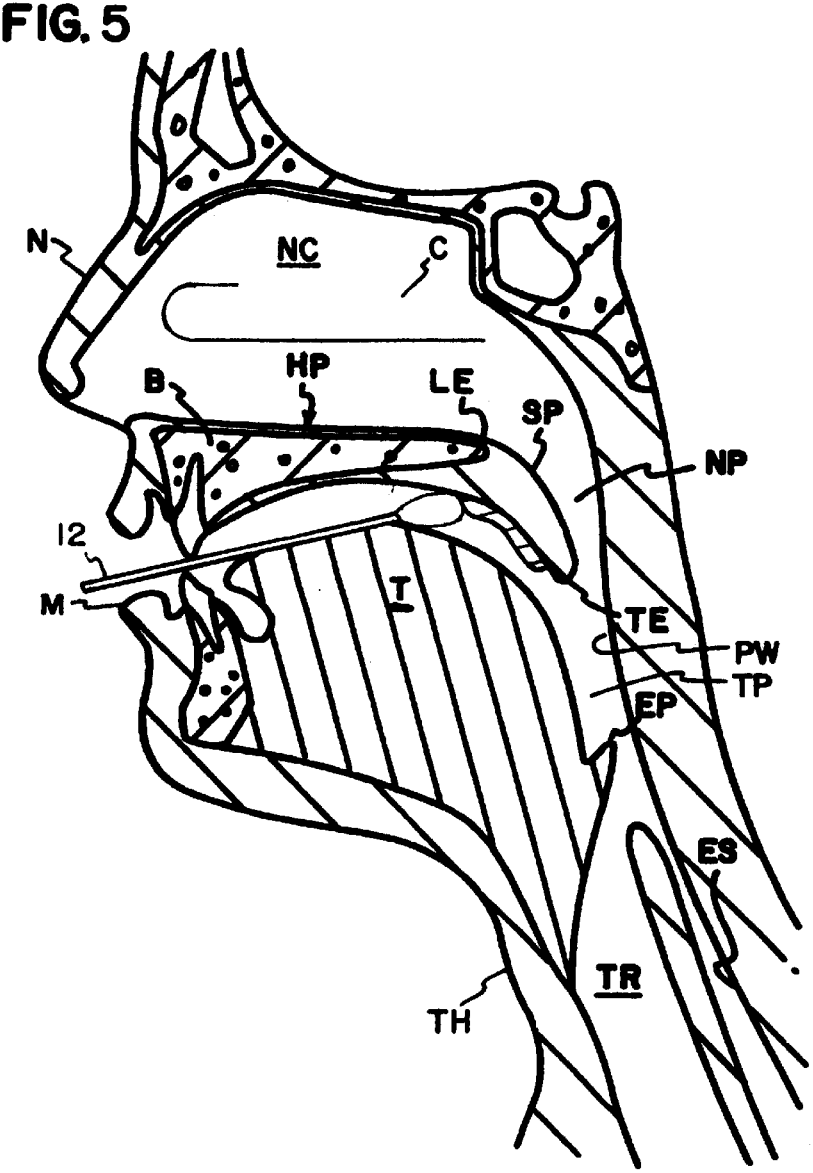
FIG. 5 is the view of FIG. 3 showing the coating applied by a swab.
Figure 6:
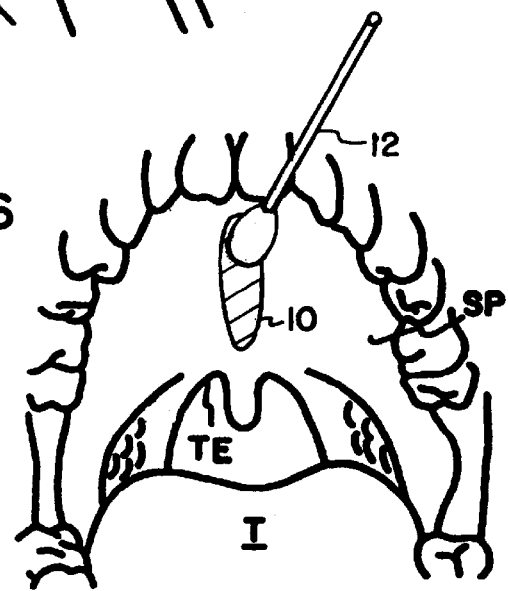
FIG. 6 is the view of FIG. 4 showing the coating applied by a swab.
Figure 7:
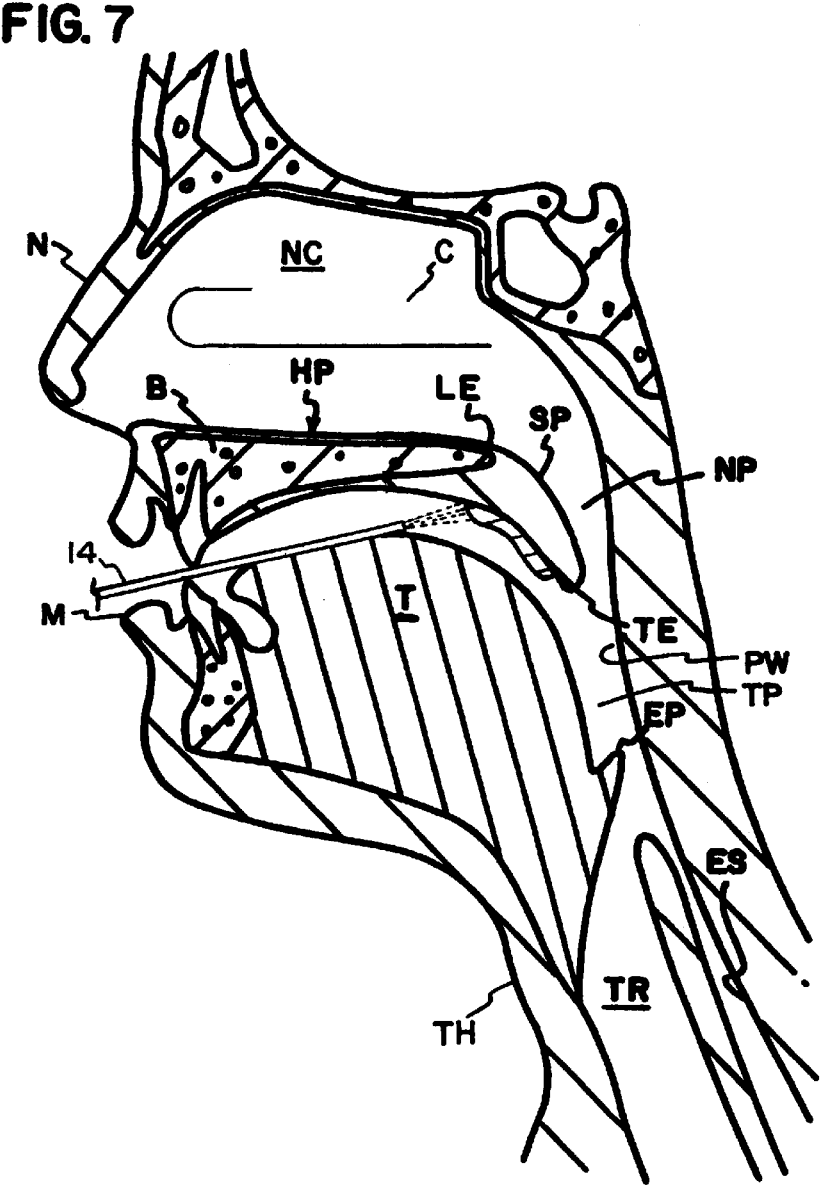
FIG. 7 is the view of FIG. 3 showing the coating applied by a spray nozzle.
Figure 8:
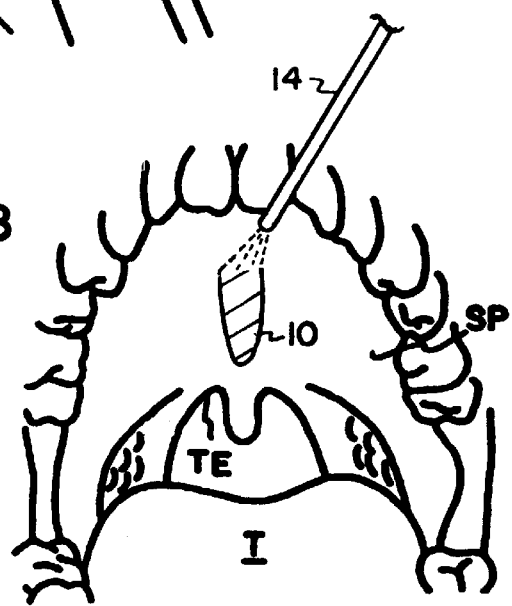
FIG. 8 is the view of FIG. 4 showing the coating applied by a spray nozzle.
Figure 10:
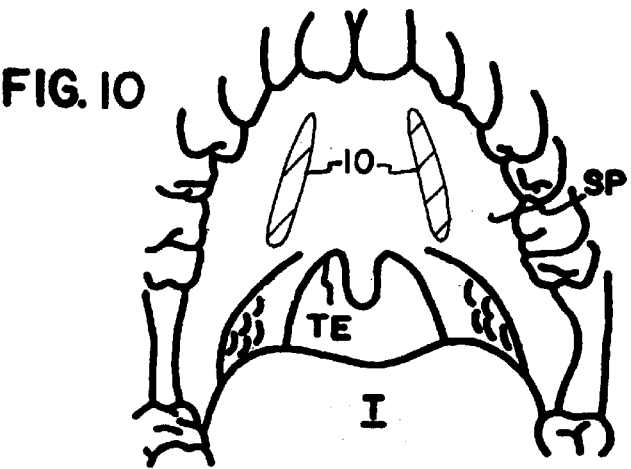
FIG. 10 is the view of FIG. 2 showing multiple, long and narrow areas of coatings on opposite sides of the middle of the soft palate.

In a first preferred embodiment, the stiffening agent is an adhering coating 10 applied in a thin coating (the thickness of the coating is exaggerated in the drawings to facilitate ease of illustration) over an area the lower surface LS of the soft palate SP (FIGS. 3 and 4). The coating 10 can be applied by swab 12 (FIGS. 5 and 6) or by a spray nozzle 14 (FIGS. 7 and 8). Preferably, the coating 10 is provided in a straight line from the trailing end TE toward the leading end LE but could be a wide area application on the lower surface LS of the soft palate SP. Multiple lines of coating 10 can be applied on opposite sides of the middle of the soft palate SP as illustrated in FIG. 10. With both the swab 12 and narrow area spay nozzle 14, the coating 10 is applied in a controlled area to be limited to a desired area of treatment. For example, if the proposed treatment is a permanent stiffening of the soft palate SP, the controllable nature of the application of coating 10 permits a coating only on the soft palate SP and not elsewhere in the mouth or throat.

It is preferred the coating be a non-toxic, bio-resorbable (or biodegradable or digestible) material. Preferably, the coating 10 adds stiffness to hinder vibration of the soft palate SP. The coating 10 may be synthetic or biological. As discussed below, the stiffening agent may be an adhesive tape, a coating 10 or a layer of hygrogel or liquid, which solidifies rapidly on the soft palate SP. Preferably, the stiffening agent is thin and flexible and of sufficient strength to permit and withstand flexing of the soft palate during swallowing and speech and resist erosion from food or drink in the mouth.

An example of coatings 10 includes cyanoacrylates. Without intending to be a limiting example, these include 2-octyl cyanoacrylate and 2-butyl cyanoacrylate. The 2-octyl cyanoacrylate is developed by Closure Medical Corp., Raleigh, N.C., USA for use to treat topical skin wounds, oral cancers and periodontal disease. It may last 1–2 weeks with faster absorbing products in development. The 2-butyl cyanoacrylate is used as a skin protectant and dental cement and is available from GluStitch, Inc., Delta, BC, Canada Biocompatible adhesives also include surgical adhesives such as those developed by CryoLife International, Inc., Kennesaw, Ga., USA whose product is composed of purified bovine serum albumin (45%) and cross-linking agent glutaraldehyde (10%). Similar formulations include natural proteins (e.g., collagen, gelatin) with aldehyde or other cross-link agents.

Such coatings may also include fibrin sealants. Examples include blood-derived products (e.g., Tisseel™ distributed by Baxter Corp., Deerfield, Ill., USA). Other examples of coatings include hydrogel coatings. An example of these include a photo-curing synthetic sealant developed by Focal, Inc., Lexington, Mass., USA which can adhere to moist or dry tissue and is highly flexible and elastic. This sealant may be absorbable over short or long terms. The sealant is currently used to treat air leaks associated with lung surgery. Other coatings include denture adhesives approved for use in humans.

From the foregoing, it can be seen there are a wide variety of adhesives and other coatings suitable for use with the present invention. The foregoing lists are intended to be illustrative and not exhaustive.

Application of a layer of coating 10 to the soft palate SP adds stiffness to the soft palate SP. A thin coating 10 is non-obtrusive.

Leaving the coating 10 in place for a limited time (16–72 hours) permits the patient (or the patient's spouse) to observe any abatement in snoring. Observation of such abatement provides enhanced confidence that more permanent treatment of the coated region will provide desired efficacy. The limited time of the coating 10 can be controlled by selecting the coating 10 for desired time of bio-resorption or can be controlled by chemical removal of the coating 10. Preferably, the coating 10 is flexible so as not to interfere with normal function of the soft palate. Preferably, the coating 10 sets to a stiffness which increases the stiffness of the soft palate. The size of the coating area and the stiffness of the coating can be varied for the coating to simulate a permanent treatment (such as a permanent stiffening implant as taught in U.S. patent application Ser. No. 09/513,432).

Figure 9:
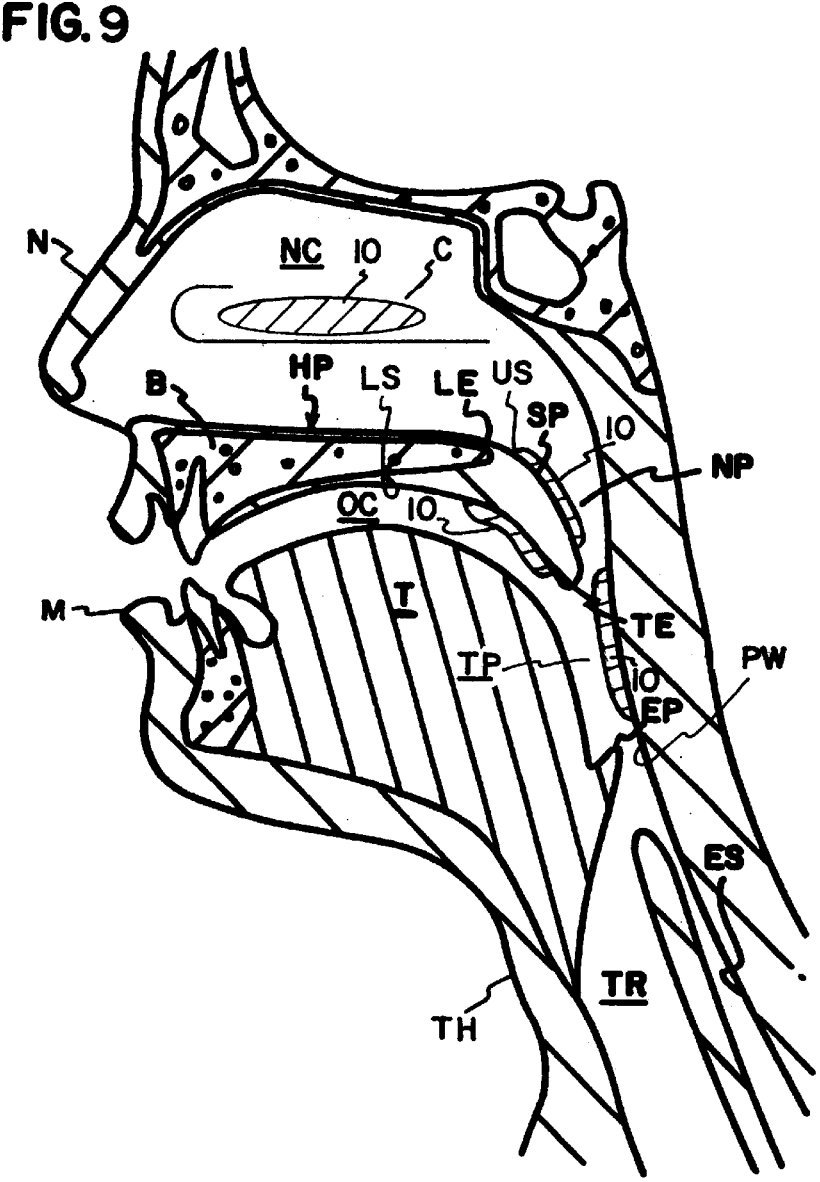
FIG. 9 is the view of FIG. 1 showing coatings applied to the upper and lower surfaces of the soft palate, the nasal concha and the pharyngeal wall.

While coating 10 of the lower surface LS of the soft palate SP has been discussed, coatings can be applied to the upper surface US of the soft palate SP (coating 10a in FIG. 9), the nasal concha (coating 10b in FIG. 9) and the pharyngeal wall (coating 10c in FIG. 9). Such coatings 10a, 10b, 10c can be applied by swab 12 or spray nozzle 14 as discussed above. As a diagnostic, it is preferred only one area is coated at a time to indicate that area's sensitivity to treatment.

Figure 11:
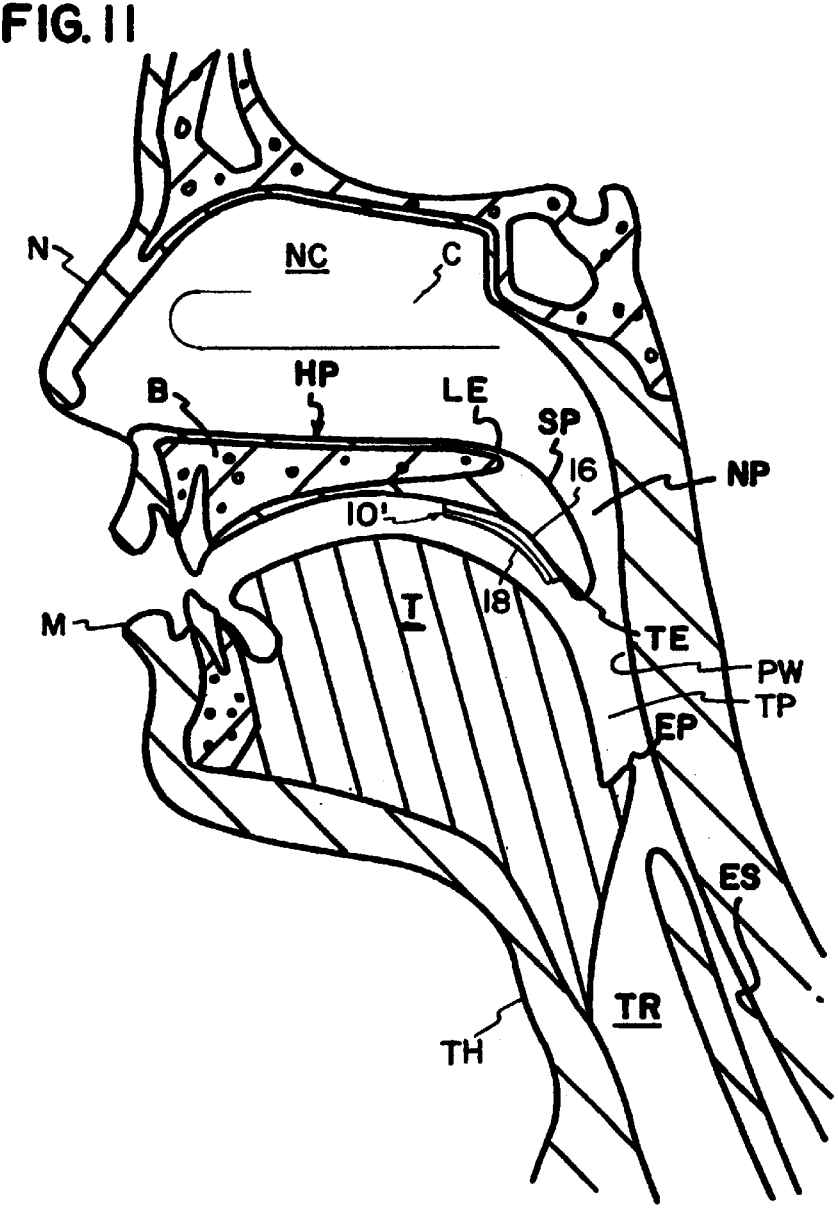
FIG. 11 is the view of FIG. 1 showing a treatment in the form of a stiffening tape applied to a lower surface of the soft palate.
Figure 12:
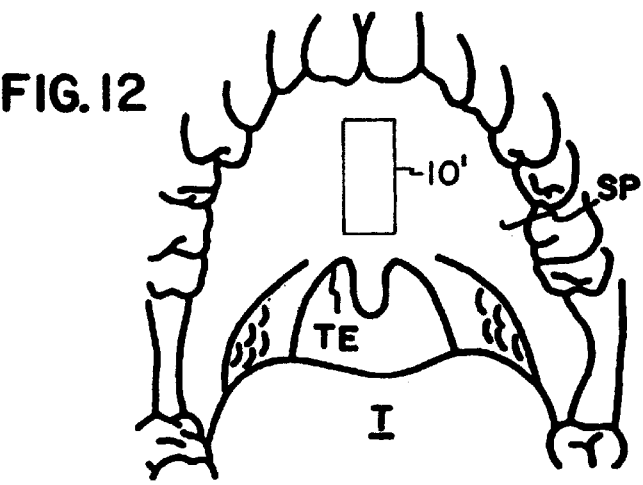
FIG. 12 is the view of FIG. 2 showing the treatment of FIG. 11.

The stiffening agent need not be a coating 10. FIGS. 11 and 12 illustrate application of a stiffening agent in the form of a tape 10' including a backing 18 and an adhesive layer 16. The stiffness of the backing 18 can be controlled as desired in manufacture to permit varying the stiffness of the stiffening agent 10' as desired. The adhesive 16 may be as described above.

The foregoing discussion has focused on a diagnostic method. The present invention can be a treatment by selecting a coating with a longer life or re-applying the coating as desired.

Through the foregoing, the present invention has been described in a preferred embodiment. It is intended that modifications and equivalents which would occur to one of ordinary skill shall be included within the scope of the present claims.

What is claimed is:

1. A diagnostic method for indicating a patient's susceptibility to treatment of snoring by stiffening a region of a naso-pharyngeal area of the patient, said method comprising:

applying a stiffening agent to an outer surface of said region of said naso-pharyngeal area;

leaving said stiffening agent on said surface for at least a temporary period of time with a stiffness of said agent on said outer surface imparting an increased stiffness to said region;

observing any abatement of snoring of the patient during said period of time.

2. A diagnostic method according to claim 1 wherein the stiffening agent is an adhering coating applied to said outer surface of said region of said naso-pharyngeal area.

3. A diagnostic method according to claim 2 wherein said coating is bio-resorbable.

4. A diagnostic method according to claim 2 wherein the coating is a cyanoacrylate.

5. A diagnostic method according to claim 2 wherein the coating is an absorbable biocompatible adhesive.

6. A diagnostic method according to claim 2 wherein the coating is a fibrin sealant.

7. A diagnostic method according to claim 2 wherein the coating is a hydrogel.

8. A diagnostic method according to claim 7 wherein the coating is photo-curing.

9. A diagnostic method according to claim 2 wherein the coating is applied by swabbing the coating on the outer surface of said region.

10. A diagnostic method according to claim 2 wherein the coating is applied by spraying the coating on the outer surface of said region.

11. A diagnostic method according to claim 2 wherein the coating is a tape adhered to the outer surface of said region.

12. A diagnostic method according to claim 1 wherein said naso-pharyngeal area is a soft palate of said patient.

13. A diagnostic method according to claim 12 wherein said outer surface is a lower surface of said soft palate.

14. A diagnostic method according to claim 12 wherein said outer surface is an upper surface of said soft palate.

15. A diagnostic method according to claim 1 wherein said naso-pharyngeal area is a nasal concha of said patient.

16. A diagnostic method according to claim 1 wherein said naso-pharyngeal area is a pharyngeal wall of said patient.

17. A method for treating snoring of a patient comprising:

identifying a region of a naso-pharyngeal area of the patient as a probable source of said snoring;

applying a stiffening agent to an outer surface of said region in an amount sufficient to abate vibration of said region with a stiffness of said agent on said outer surface imparting an increased stiffness to said region.

* * * * *